US00PP12891P2

(12) United States Plant Patent
Vandenberg

(10) Patent No.: US PP12,891 P2
(45) Date of Patent: Aug. 27, 2002

(54) CHRYSANTHEMUM PLANT NAMED 'LUCKY SUERTE'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 69 days.

(21) Appl. No.: 09/756,360

(22) Filed: Jan. 9, 2001

(51) Int. Cl.[7] ..... A01H 5/00
(52) U.S. Cl. ..... Plt./296
(58) Field of Search ..... Plt./296, 295

(56) References Cited

U.S. PATENT DOCUMENTS 4,616,099 A * 10/1986 Sparkes ..... 47/58
PP10,754 P * 1/1999 VandenBerg ..... Plt./296

OTHER PUBLICATIONS

Broertjes, et al., 1980, "A mutant of a mutant of a . . . Irradiation of progressive radiation–induced mutants in a mutation breeding programme with *Chrysanthemum morifolium*", Euphytica 29: 525–530.*

Gosling, ed. 1979,, "The Chrysanthemum Manual—6$^{th}$ edition", The National Chrysanthemum Society, London, Essex Telegraph Press, Ltd., pp. 329–336.*

Broertjes, et al., 1978, "Application of Mutation Breeding Methods in The Improvement of Vegetatively Propagated Crops", Elsevier Sci. Pub. Co., New York, pp. 162–175.*

Searle, et al., 1968, "Chrysanthemums The Year Round", Blanford Press, London, pp. 27–29, 320–327.*

Chan, 1966, "Chrysanthemum and rose mutations induced by x–rays", Am. Soc. Hort. Sci. Proc., pp. 613–620.*

Broertjes, 1966, "Mutation breeding of chrysanthemums", Euphytica, 15: 156–162.*

Dowrick, et al., 1966, "The induction of mutations in Chysanthemum using x– and gamma radiation", Euphytica, 15: 204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Lucky Suerte', characterized by its daisy-type inflorescences that are about 7.3 cm in diameter; attractive vibrant orange ray and bright yellow disc florets; very freely flowering habit with numerous inflorescences per stem; early flowering, response time about 54 days; dark green foliage; strong stems; and good postproduction longevity with inflorescences maintaining good substance and color for at least four weeks in an interior environment.

2 Drawing Sheets

BACKGROUND OF THE INVENTION

The present invention relates to a new and distinct cultivar of Chrysanthemum plant, botanically known as *Chrysanthemum×morifolium* and hereinafter referred to by the name 'Lucky Suerte'.

The new Chrysanthemum is a product of a mutation induction breeding program conducted by the Inventor in Salinas, Calif. The objective of the program is to create new Chrysanthemum cultivars with desirable inflorescence form and floret colors, good substance, and good postproduction longevity.

The new Chrysanthemum is a naturally-occurring whole plant mutation of a proprietary induced mutation that originated by exposing unrooted cuttings of the Chrysanthemum cultivar Orange Suerte, disclosed in U.S. Plant Pat. No. 10,754, to X-ray radiation. The new Chrysanthemum was discovered and selected by the Inventor as a single flowering plant within a population of plants of the irradiated selection in April, 1997, in Salinas, Calif. The selection of this plant was based on its desirable inflorescence form and floret colors and good postproduction longevity.

Asexual reproduction of the new Chrysanthemum by terminal cuttings taken in a controlled environment in Salinas, Calif., has shown that the unique features of this new Chrysanthemum are stable and reproduced true to type in successive generations.

SUMMARY OF THE INVENTION

The cultivar Lucky Suerte has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Lucky Suerte'. These characteristics in combination distinguish 'Lucky Suerte' as a new and distinct cultivar:

1. Large daisy-type inflorescences that are about 7.3 cm in diameter.

2. Attractive vibrant orange-colored ray florets and bright yellow-colored disc florets.

3. Very freely flowering with numerous inflorescences per stem.

4. Early flowering, response time is about 54 days.

5. Dark green foliage.

6. Strong and thick stems.

7. Good postproduction longevity with inflorescences maintaining good substance and color for at least four weeks in an interior environment.

Compared to plants of the cultivar Orange Suerte, plants of the new Chrysanthemum have shorter flowering stems and ray florets are more vibrant orange in color.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Lucky Suerte' grown as a spray-type cut Chrysanthemum.

The photograph on the second sheet comprises a close-up view of typical inflorescences of 'Lucky Suerte'.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate commercial practice in a double-layer polyethylene-covered greenhouse. Two-week old rooted cuttings were planted on Jun. 7, 2000 and received 12 long day/short nights followed by short day/long nights until flowering. Plants were grown as single-stem cut chrysanthemums. During the production time, the following environmental conditions were measured: day temperatures, 18 to 27° C.; night temperatures, 16 to 18° C.; and light levels, 2,000 to 4,000 foot-candles. Measurements and numerical values represent averages for six to ten typical flowering stems and were taken during the week of Aug. 21, 2000.

Botanical classification: *Chrysanthemum×morifolium* cultivar Lucky Suerte.

Commercial classification: Daisy spray-type cut Chrysanthemum.

Parentage: Naturally-occurring whole plant mutation of a proprietary *Chrysanthemum×morifolium* induced mutation, not patented.

Progpagation:

*Type*.—Terminal tip cuttings.

*Time to rooting* .—About seven to ten days with soil temperatures of 21° C.

*Root description*.—Fine, fibrous and well-branched.

Plant description:

*Appearance*.—Herbaceous daisy spray-type cut flower.

*Flowering stem description*.—Aspect: Erect. Length: About 88.9 cm. Diameter: About 7 mm. Texture: Pubescent. Color: 146A.

*Foliage description:* Arrangement: Alternate. Length: About 9.2 cm. Width: About 6.7 cm. Apex: Cuspidate to mucronate. Base: Mostly truncate. Margin: Palmately lobed; sinuses convergent to divergent. Texture: Upper and lower surfaces pubescent. Veins prominent on lower surface. Color: Young foliage upper surface: Much darker than 147A. Young foliage lower surface: Close to 147A. Mature foliage upper surface: Darker than 147A; venation, 147A to 147B. Mature foliage lower surface: Close to 147B; venation, close to 146A. Petiole: Length: About 1.9 cm. Diameter: About 4 mm. Color: Upper surface: Close to 146B. Lower surface: Close to 146B to 146C.

Flowering description:

*Appearance*.—Daisy spray-type inflorescence form with elongated oblong-shaped ray florets. Inflorescences borne on terminals, arising from leaf axils. Disc and ray florets arranged acropetally on a capitulum.

*Flowering response*.—Under natural conditions, plant flowers in the autumm/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 54 days later.

*Postproduction longevity*.—In an interior environment, flowering stems will maintain good color and substance for at least four weeks in an interior environment after one week of cool storage.

*Quantity of inflorescences*.—Freely flowering with about 16 inflorescences per flowering stem.

*Inflorescence size*.—Diameter: About 7.3 cm. Depth (height): About 2.5 cm. Diameter of disc: About 1.5 cm. Diameter of receptacle: About 7 mm.

*Ray florets*.—Shape: Elongated oblong. Length: About 3.8 cm. Width: About 1 cm. Corolla tube length: About 6 mm. Corolla tube diameter: About 1.5 mm. Apex: Rounded, mammillate or emarginate. Base: Attenuate. Margin: Entire. Texture: Smooth, satiny, glabrous; longitudinally ridged. Aspect: Initially incurved and concave becoming mostly flat with subsequent development. Aspect: Initially upright; when mature, about 70° from vertical. Number of ray florets per inflorescence: About 75 arranged in about four rows. Color: When opening, upper surface: Yellow ground color, close to 9A; faintly overlain with red, close to 45A to 46A to 53A; overall tonality, close to 169A to 169B. When opening, lower surface: Yellow ground color, close to 9C, very faintly underlain with red, close to 53A; overall tonality, close to 162A. Mature, upper surface: Yellow ground color, close to 9A; faintly overlain with red, close to 45A to 46A to 53A; overall tonality, close to 169B to 168A; fading to close to 168B with subsequent development. Mature, lower surface: Yellow ground color, close to 9C; very faintly underlain with red, close to 53A; overall tonality, close to 162A.

*Dics florets*.—Shape: Tubular, slightly flared at apex. Length: About 6.5 mm. Width: Apex: About 1.5 mm. Base: About 1 mm. Number of disc florets per inflorescence: Numerous, typically about 139. Color: Immature: Initially 144A, then 145A to 154A. Mature: Apex: 9A. Mid-section: Close to 154D. Base: 155D.

*Peduncle*.—Strength: Strong. Aspect: Angled about 45° from vertical. Length: First peduncle: About 7.7 cm. Fourth peduncle: About 9.3 cm. Seventh peduncle: About 13.8 cm. Diameter: About 3 mm. Texture: Very fine pubescence. Color: 146A to 144A.

*Reproductive organs*.—Androecium: Present on disc florets only. Anther color: 9A. Amount of pollen: Moderate. Color: 15A. Gynoecium: Present on both ray and disc florets.

*Seed*.—Seed production has not been observed.

Disease resistance: Resistance to pathogens common to Chrysanthemums has not been observed on plants grown under commercial conditions.

Temperature tolerance: Plants of the new Chrysanthemum have demonstrated good tolerance to night temperatures as low as 5° C. and day temperatures as high as 40° C.

It is claimed:

1. A new and distinct cultivar of Chrysanthemum plant named 'Lucky Suerte', as illustrated and described.

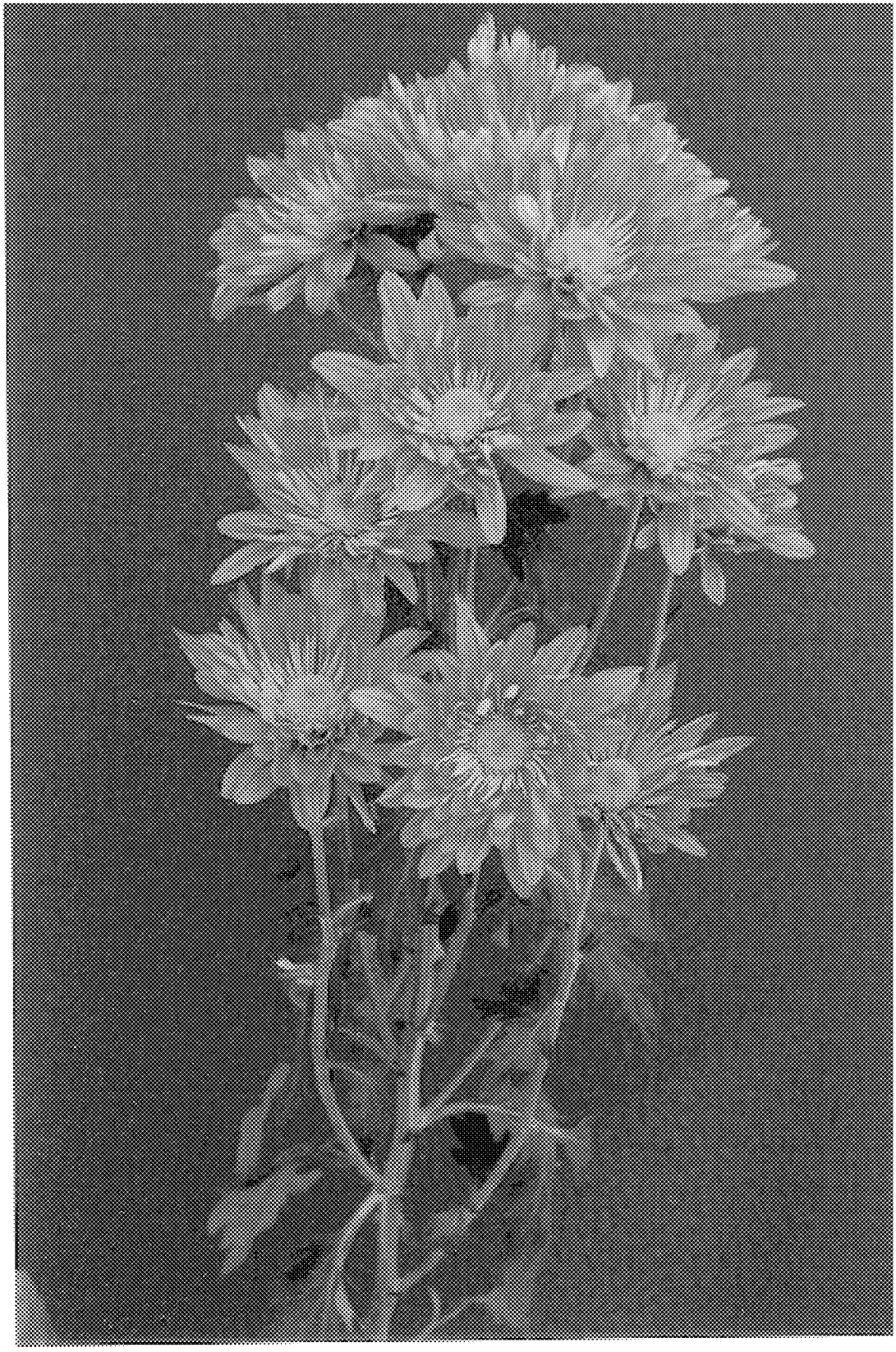

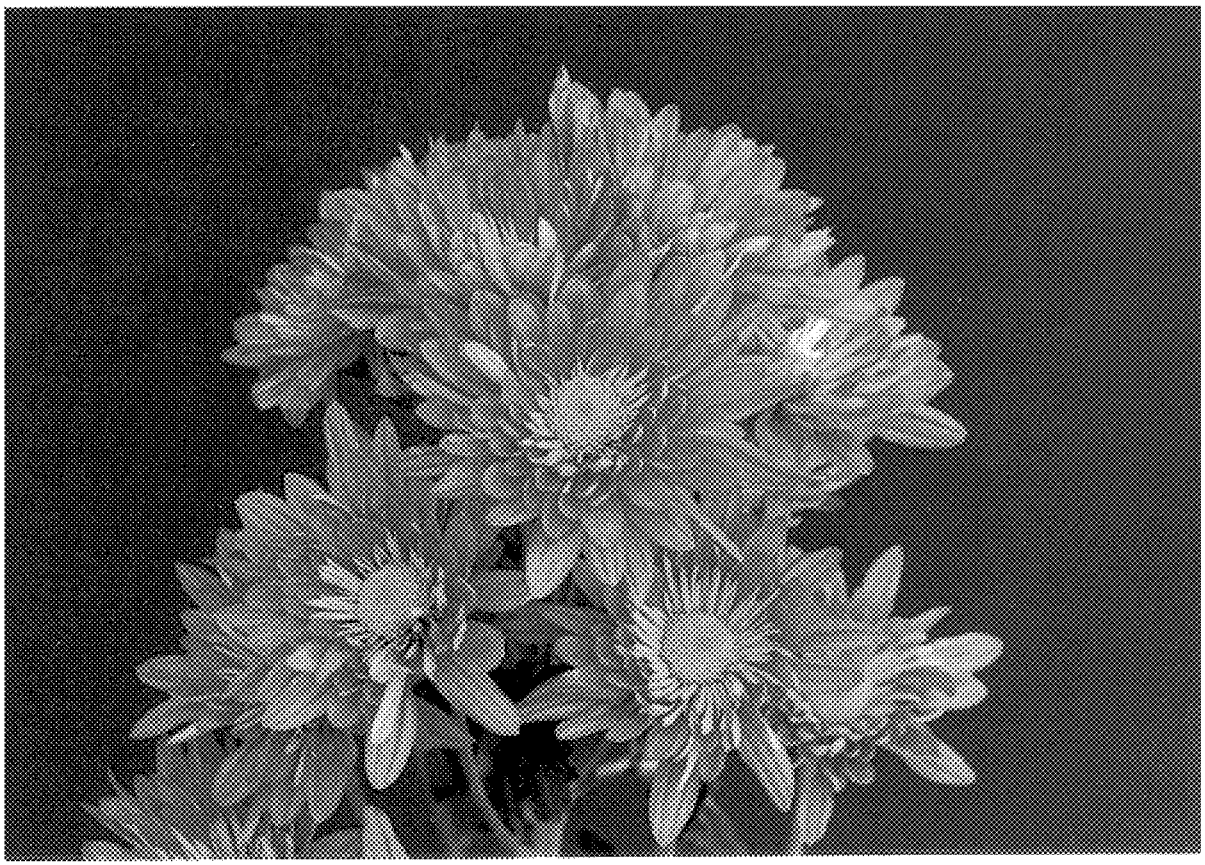

* * * * *